(12) United States Patent
Dasgupta et al.

(10) Patent No.: US 6,890,372 B2
(45) Date of Patent: May 10, 2005

(54) DENUDER ASSEMBLY FOR COLLECTION AND REMOVAL OF SOLUBLE ATMOSPHERIC GASES

(75) Inventors: Purnendu K. Dasgupta, Lubbock, TX (US); Kavin J. Morris, Ransom Canyon, TX (US); Jianzhong Li, Lubbock, TX (US)

(73) Assignee: Dionex Corporation, Sunnyvale, CA (US)

( * ) Notice: Subject to any disclaimer, the term of this patent is extended or adjusted under 35 U.S.C. 154(b) by 16 days.

(21) Appl. No.: 10/651,057

(22) Filed: Aug. 27, 2003

(65) Prior Publication Data

US 2005/0045032 A1 Mar. 3, 2005

(51) Int. Cl.$^7$ .............................. B01D 53/22
(52) U.S. Cl. ..................... 95/44; 95/214; 96/5; 96/101; 96/413; 73/31.07
(58) Field of Search .............................. 95/43, 44, 45, 95/214; 96/4, 5, 101, 267, 272, 326, 413; 73/31.07

(56) References Cited

U.S. PATENT DOCUMENTS

| | | | |
|---|---|---|---|
| 4,750,918 A | * | 6/1988 | Sirkar ........................ 95/44 |
| 4,999,098 A | | 3/1991 | Pohl et al. |
| 5,281,254 A | * | 1/1994 | Birbara et al. ................ 95/44 |
| 5,302,191 A | * | 4/1994 | Koutrakis et al. ............ 95/285 |
| 6,033,459 A | | 3/2000 | Hase |
| 6,156,096 A | * | 12/2000 | Sirkar ........................ 95/44 |
| 6,497,136 B2 | | 12/2002 | Satou |
| 6,506,345 B1 | | 1/2003 | Lee et al. |

OTHER PUBLICATIONS

Allegrini et al., *Carbon–coated annular denuders and ion chromatographic measurements for the determination of nitrogen–containing species ($NO_{2\ and\ NO_y}$) in remote atmospheres*, J. Chromatography A, 1999, 846, pp. 265–268.

Benner et al., *Comparison and Annular Denuder and Filter Pack Collection of $HNO_3(g)$, $SO_2(g)$, and Particulate-Phase Nitrate, Nitrite and Sulfate in the South–West Desert*, Atmospheric Environment, 1991, 25A, pp. 1537–1545.

Boring et al., *Field Measurement of Acid Gases and Soluble Anions in Atmospheric Particulate Matter Using a Parallel Plate Wet Denuder and an Alternating Filter–Based Automated Analysis System*, Anal. Chem., 2001, 74, pp. 1256–1266.

Boring et al., *Wet effluent parallel plate diffusion denuder coupled capillary ion chromatograph for the determination of atmospheric trace gases*, Talanta, 1999, 48, pp. 675–684.

(Continued)

Primary Examiner—Frank M. Lawrence
(74) Attorney, Agent, or Firm—Dorsey & Whitney LLP; David J. Brezner; Victor E. Johnson

(57) ABSTRACT

A denuder assembly is adapted for the collection and removal of a gaseous analyte from a sample gas. The denuder includes a housing including an internal cavity, a sample gas inlet fluidly coupled with a sample gas source, a denuder liquid inlet fluidly coupled with a denuder liquid source, a barrier sheet extending across the internal cavity and separating the internal cavity into a liquid reservoir and a gas flow-through channel fluidly coupled with and downstream of the sample gas inlet, and a denuder liquid disposed in the liquid reservoir and permeating the barrier sheet to coat the gas-channel surface of the barrier sheet thereby allowing the denuder liquid on the gas-channel surface to contact the sample gas flowing within the gas flow-through channel and allowing the analyte to diffuse through the barrier sheet into the liquid reservoir.

30 Claims, 8 Drawing Sheets

OTHER PUBLICATIONS

Dasgupta et al., *A Multiple Parallel Plate Wetted screen Diffusion Denuder for High–Flow Air Sampling Applications*, Anal. Chem. 1997, 67, 24, pp. 5018–5023.

Dasgupta, *A Diffusion Scrubber for the Collection of Atmospheric Gases*, Atmospheric Environment, 1984, 18, No. 8, pp. 1593–1599.

Dasgupta, *Automated diffusion–based collection and measurement of atmospheric trace gases*, Comprehensive Analytical Chemistry XXXVII, 2002, Chap. 5, pp. 99–.

De Santis, *Comment on Wet Effluent Denuder Coupled Liquid/Ion Chromatography Systems: Annular and Parallel Plate Denuders*, Anal. Chem., 1994, 66, pp. 3503–3504.

Fan et al., *Continuous Automated Determination of Atmospheric Formaldeyhde at the Parts Per Trillion Level*, Anal. Chem., 1994, 66, pp. 551–556.

Fitz et al., *A Fabric Denuder for Sampling Semi–Volatile Species*, J. Air & Waste Manage. Assoc., 2000, 50, pp. 981–992.

Genfa et al., *Hematin as a Peroxidase Substitute in Hydrogen Peroxide Determinations*, Anal. Chem., 1992, 64, pp. 517–522.

Hwang et al., *Thermodynamics of the Hydrogen Peroxide-Water System*, Environ. Sci. Technol., 1985, 19, 3, pp. 255–258.

Jaeschke et al., *Phase Partitioning of Ammonia and Ammonium in a Multiphase System Studied Using a New Vertical Wet Denuder Technique*, Atmospheric Environment, 1998, 32, 3, pp. 365–371.

Keuken et al., *Simultaneous Sampling of $NH_3$, HCl, $SO_2$ and $H_2O_2$ in Ambient Air by a Wet Annular Denuder System*, Atmospheric Environment, 1988, 22, 11, pp. 251–2548.

Li et al., *Measurement of Atmospheric Formaldehyde with a Diffusion Scrubber and Light–Emitting Diode—Liquid Core Waveguide Based Fluorometry*, Field Anal. Chem. & Tech., 2001, 5(1–2), pp. 2–12.

Li et al., *Measurement of Atmospheric Hydrogen Peroxide and Hydroxymethyl Hydroperoxide with a Diffusion Scrubber and Light–Emitting Diode—Liquid– Core Waveguide Based Fluorometry*, Anal. Chem:, 2000, 72, 21, 5338–5347.

Li et al., *Measurement of gaseous hydrogen peroxide with a liquid– core waveguide chemiluminescence detector*, Analytica Chimica Acta, 2001, 442, 63–70.

Li et al., *Pulsed Excitation Source Multiplexed Fluorometry for the Simultaneous Measurement of Multiple Analytes. Continuous Measurement of Atmospheric Hydrogen Peroxide and Methyl Hydroperoxide*, Anal. Chem., 2003, 75, pp. 1203–1210.

Mader et al., *Sampling Atmospheric Carbonaceous Aerosols Using a Particle Trap Impactor/Denuder Sampler*, Environ. Sci. Technol., 2001, 35, pp. 4857–4867.

Philips et al., *A Diffusion Scrubber for the Collection of Gaseous Nitric Acid*, Separation Sci. & Tech., 1987, 22(4), pp. 1255–1267.

Rosman et al., *Laboratory and field investigations of a new and simple design for the parallel plate denuder*, Atmospheric Environment, 2001, 35, pp. 5301–5310.

Sakamoto et al., *Development of an automatic continuous anlayzer for water–soluble gases in air by combining an artificial lung with an ion chromatograph*, Atmospheric Environment, 2002, 36, pp. 441–448.

Simon et al., *Continuous Automated Measurement of Gaseous Nitrous and Nitric Acids and Particulate Nitrite and Nitrate*, Environmental Sci. & Tech., 1995, 29, pp. 1534–1541.

Simon et al., *Continuous Automated Measurement of the Soluble Fraction of Atmospheric Particulate Matter*, Analytical Chemistry, 1995, 67, 1, pp. 71–78.

Simon et al., *Wet Effluent Denuder Coupled Liquid/Ion Chromatography Systems: Annular and Parallel Plate Denuders*, Anal. Chem. 1993, 65, pp. 1134–1139.

Toda et al., *Fluorometric Field Instrument for Continuous Measurement of Atmospheric Hydrogen Sulfide*, Anal. Chem., 2001, 73, pp. 5716–5724.

Zhang et al., *Design of a Straight inlet Diffusion Scrubber, Comparison of Particle Transmission with Other Collection Devices and Characterization for the Measurement of Hydrogen Peroxide and Formaldehyde*, Atmospheric Environment, 1991, 25A, No. 12, pp. 2717–2729.

Zhang et al., *Evaporative Losses of Fine Particulate Nitrates During Sampling*, Atmospheric Environment, 1992, 26A, No. 18, pp. 3305–3312.

Zhang et al., *Theoretical Analysis of Evaporative Losses of Adsorbed or Absorbed Species during Atmospheric Aerosol Sampling*, Environ. Sci. Technol., 1991, 25, pp. 456–459.

* cited by examiner

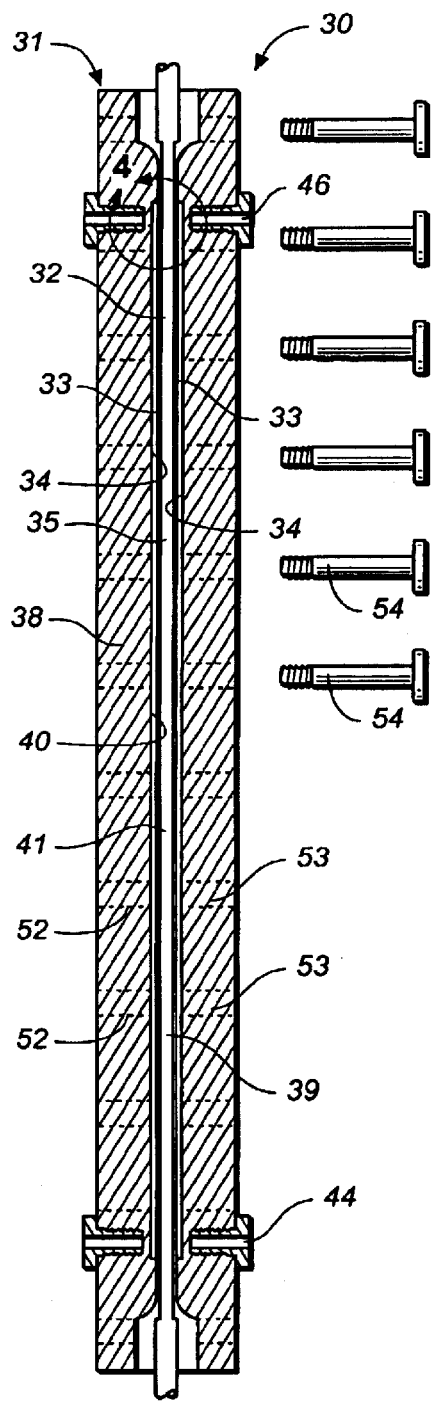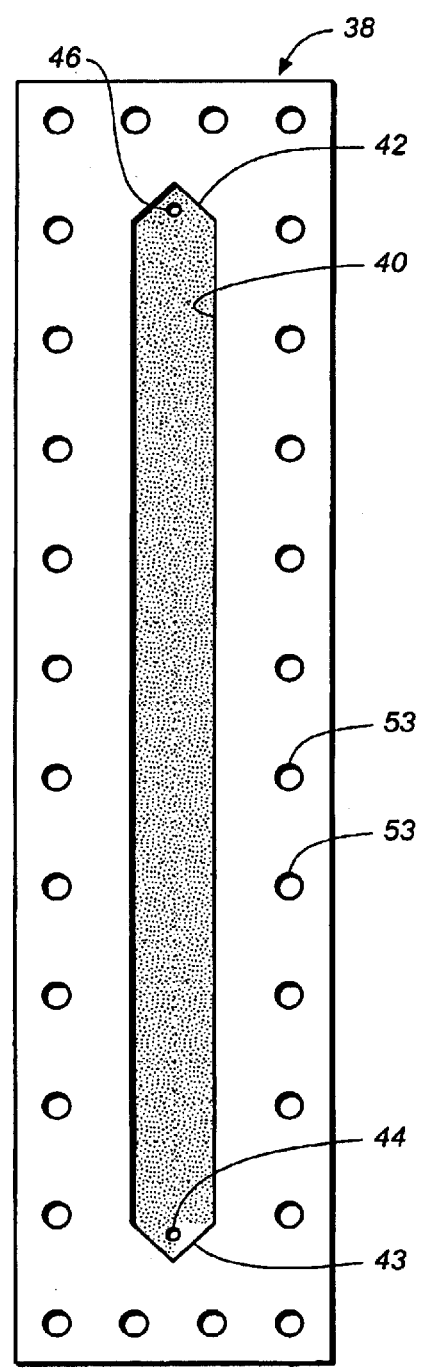
FIG._1          FIG._2

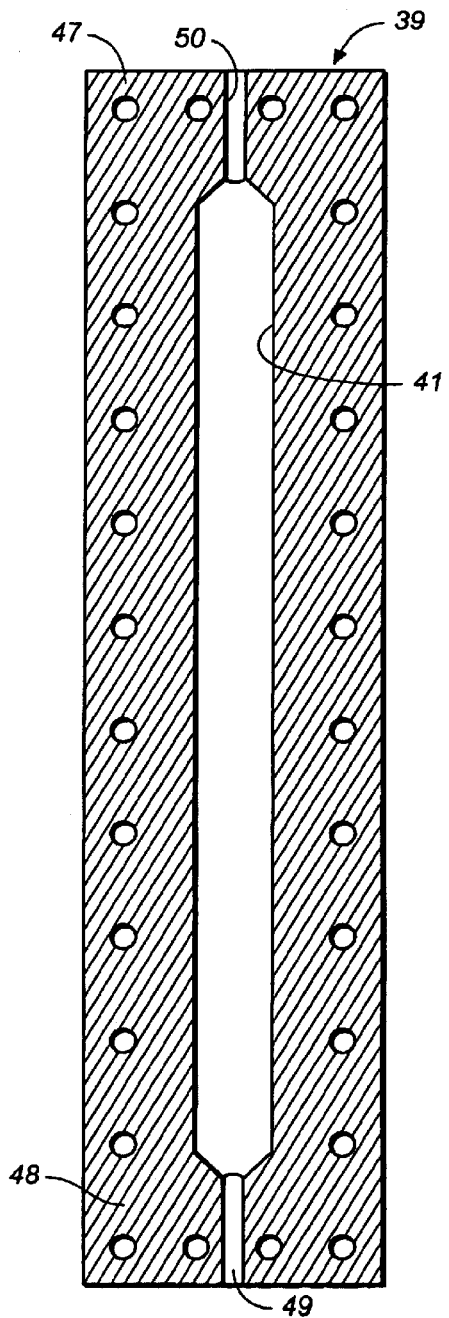
FIG._3
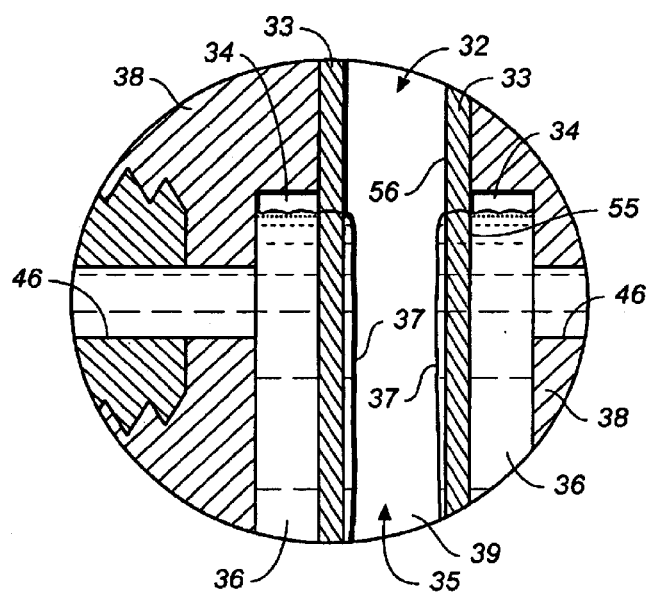
FIG._4

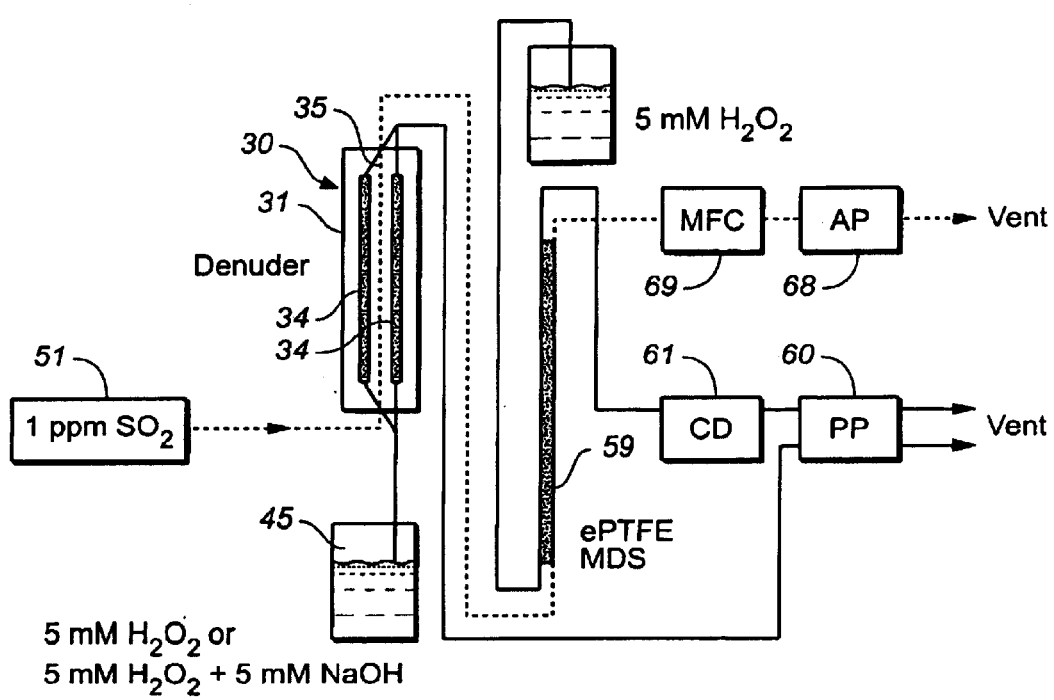
FIG._5
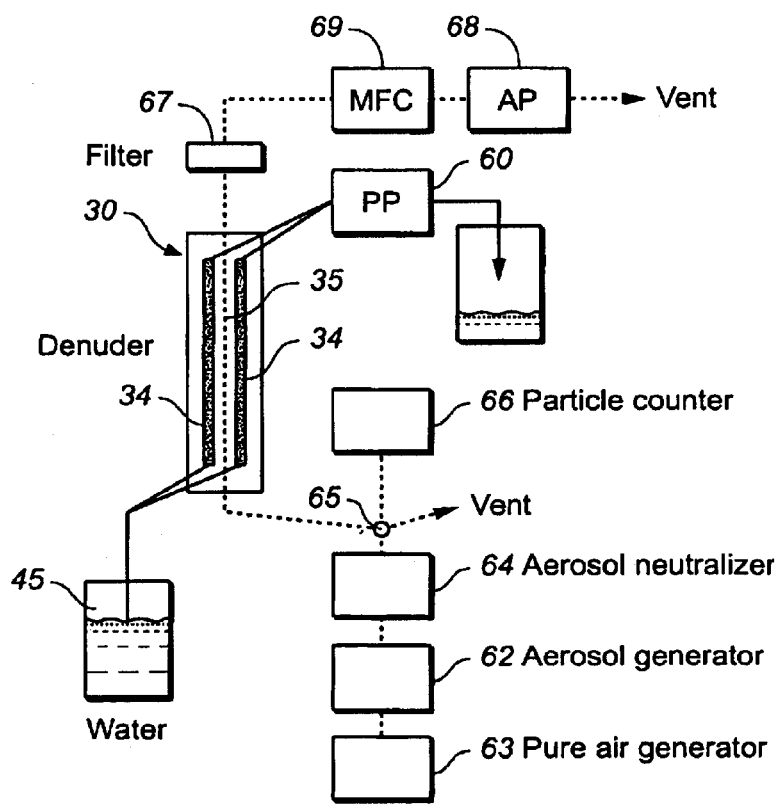
FIG._6

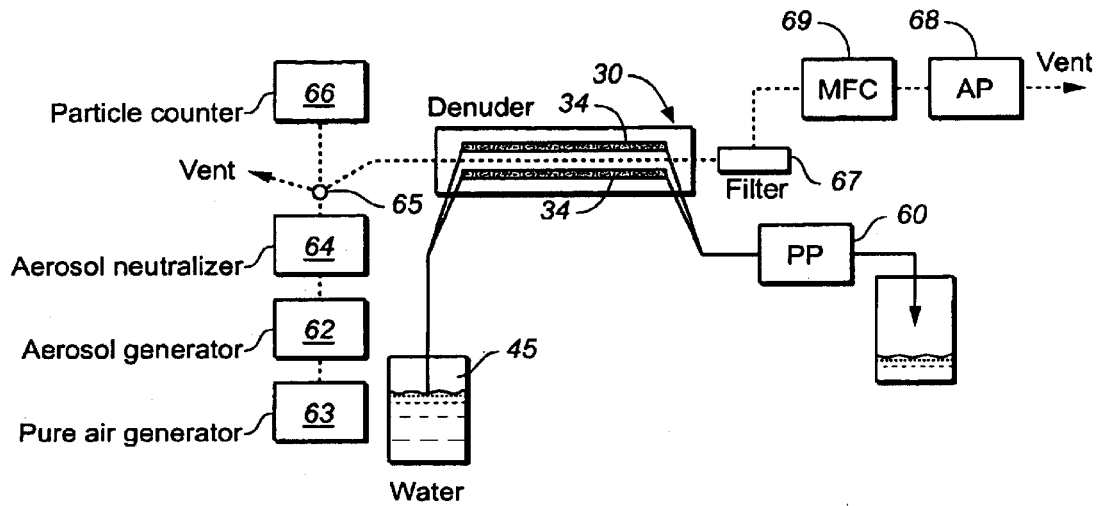
FIG._7
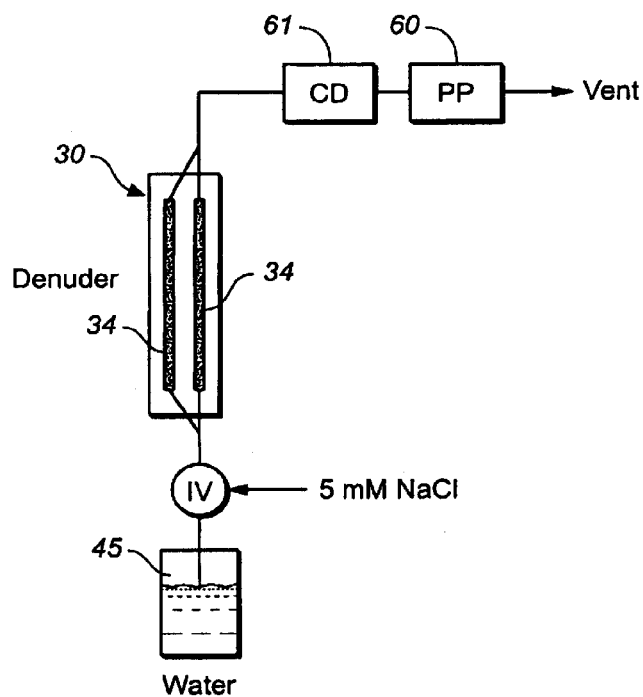
FIG._8

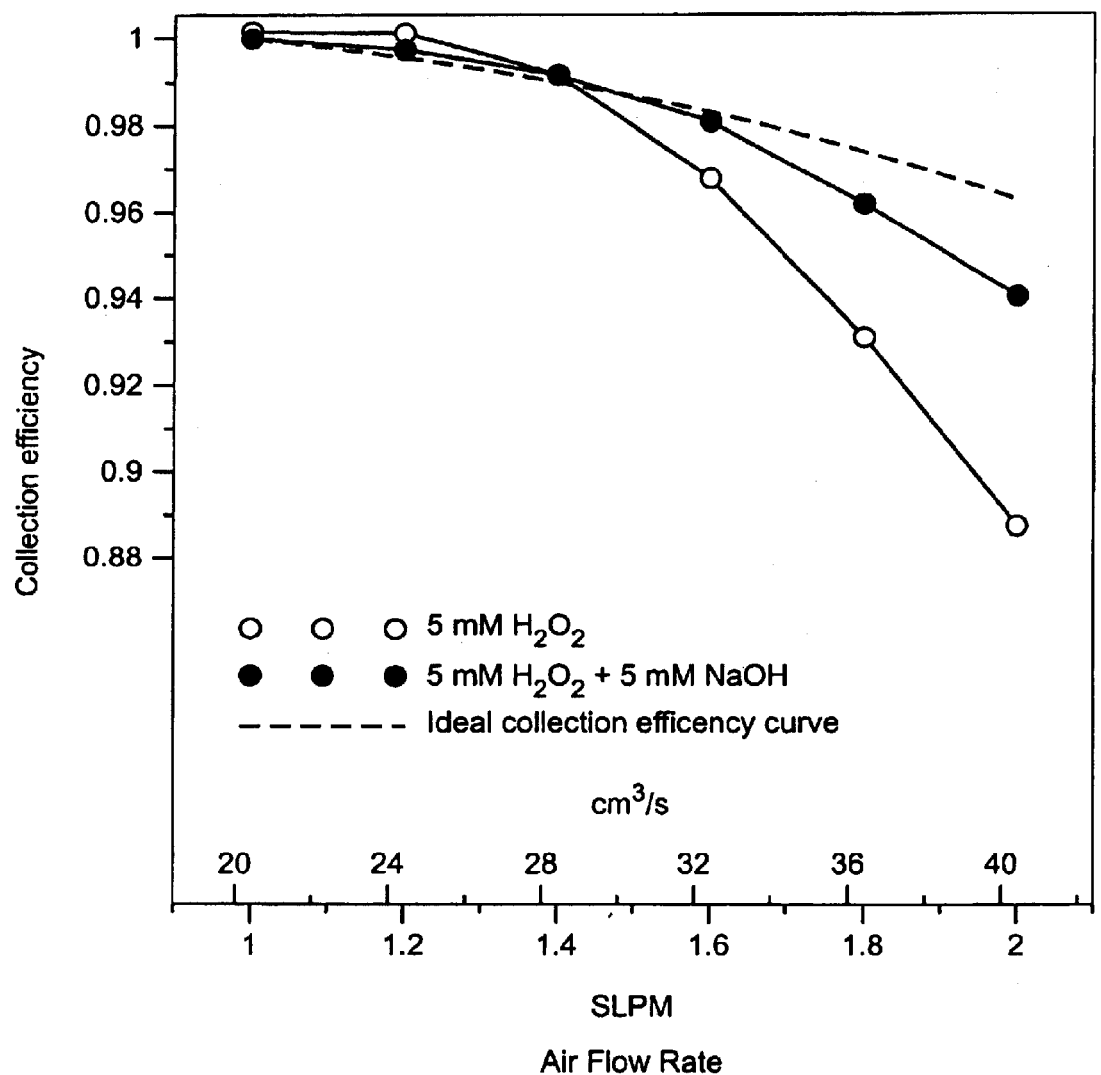
FIG._9

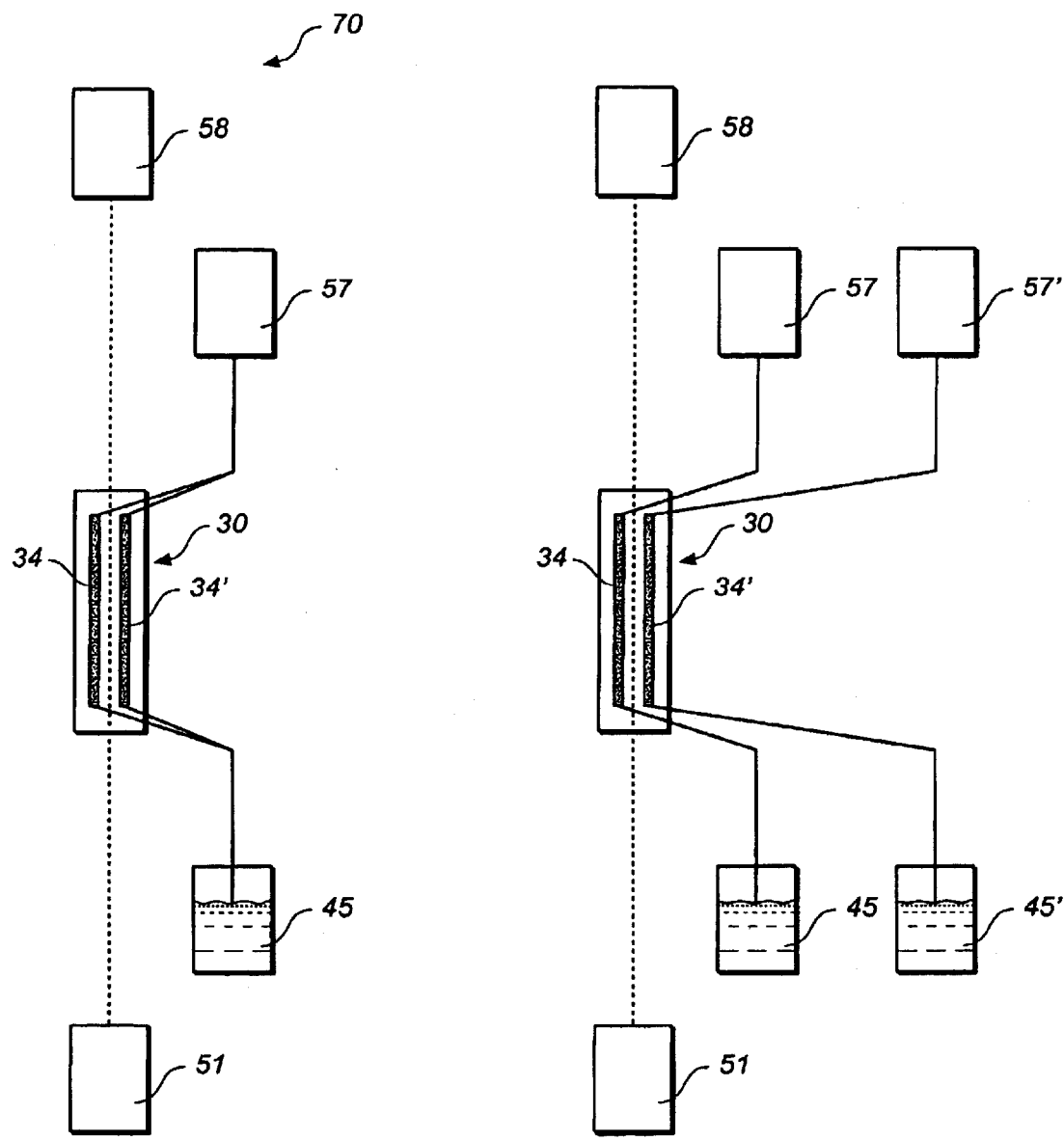
FIG._10   FIG._11

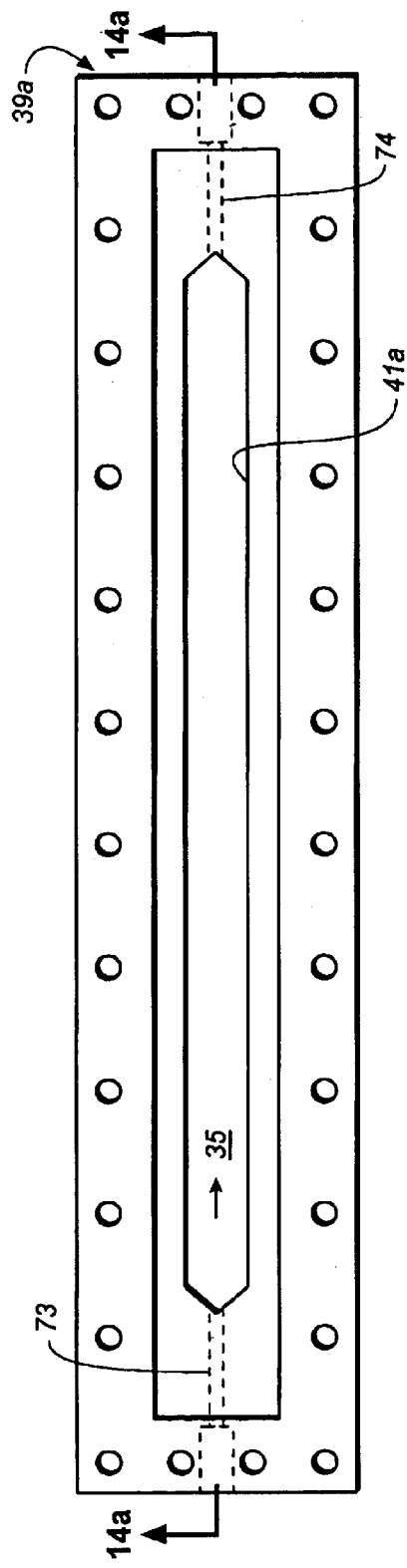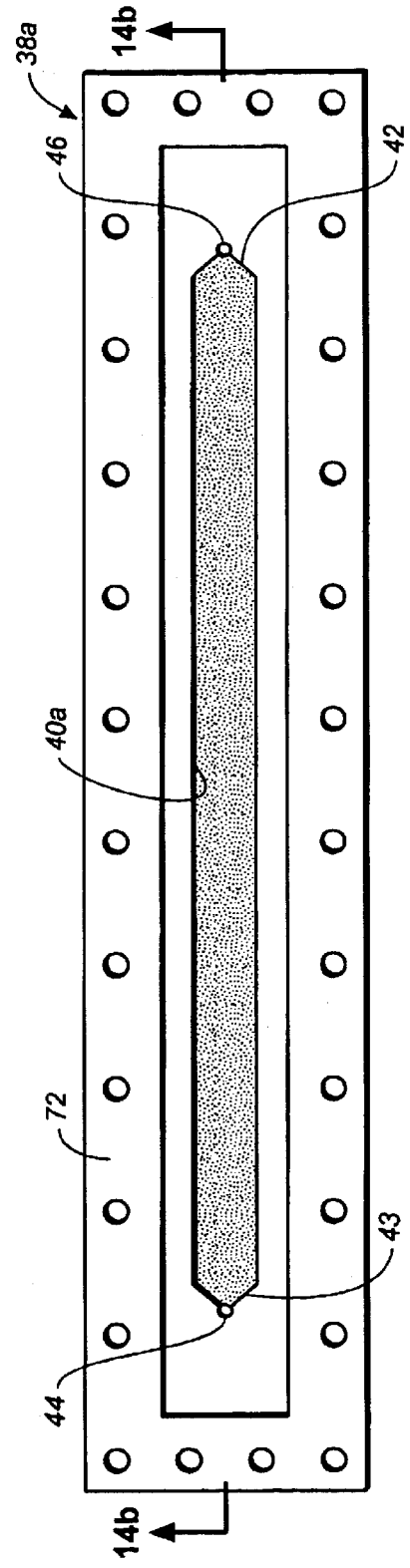

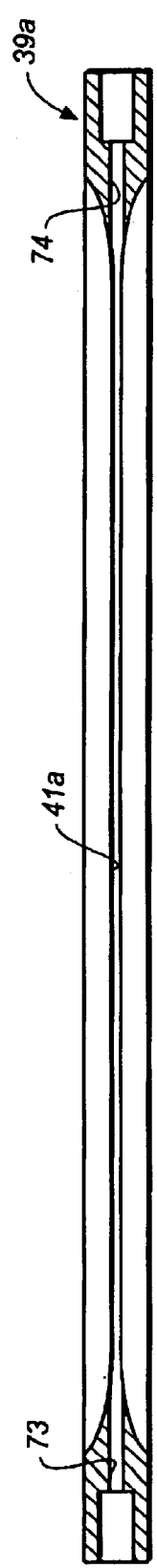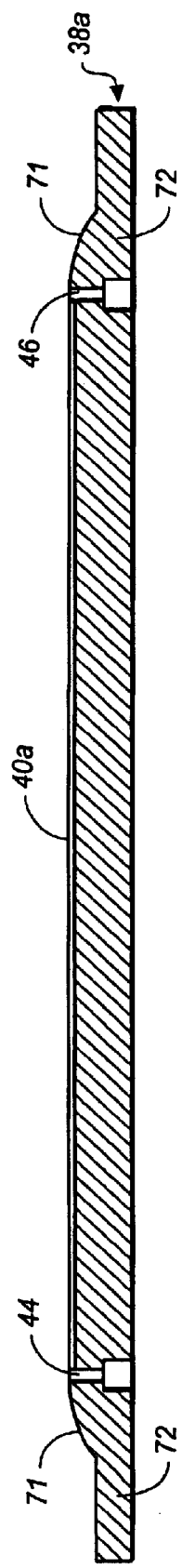

DENUDER ASSEMBLY FOR COLLECTION AND REMOVAL OF SOLUBLE ATMOSPHERIC GASES

BACKGROUND OF THE INVENTION

1. Field of the Invention

This invention relates, in general, to a denuder assembly for the collection and removal of soluble atmospheric gases and more particularly to a denuder assembly utilizing a wetted membrane and methods for its use.

2. Description of Related Art

Diffusion denuder techniques have largely replaced filter-based methods for the collection of atmospheric trace gases. The selective removal of gases from gas-particle mixtures by a denuder exploits the large difference in diffusion coefficients between gases and particles. When an air sample is drawn through a denuder under laminar flow condition, gas molecules of the air sample diffuse to the walls of the denuder and are captured, while very small particles diffuse too slowly for them to reach the wall. Although a variety of coated denuders have been used for the collection and removal of atmospheric gases, known processes utilizing such coated denuders have several disadvantages as such known processes are laborious, time-consuming, and contamination-prone as the processes involve coating, drying, and washing denuder tubes.

In contrast, wet denuders depend on direct gas-liquid contact. In known wet denuders, a sample gas flow is typically surrounded by a flowing collector liquid. The wettability of a denuder surface of a wet denuder is a critical factor in maintaining a thin liquid film exposed to the sampled air, which typically flows at a much greater rate and generally countercurrent to the liquid flow. Such continuously wetted denuders have been reported in the last 15 years. For example, Keuken et al. reported an early wetted denuder having an annular design and which rotates around its axis, operating in a horizontal configuration, in order to keep the annulus uniformly wet. See Menno P. Keuken et al, *Simultaneous Sampling Of $NH_3$, $HNO_3$, HCl, $SO_2$ And $H_2O_2$ In Ambient Air By A Wet Annular Denuder System*, Atmospheric Environment, vol. 22, no. 11, pp. 2541–2548 (1988). With such an annular denuder, collection efficiency for many water-soluble gases is near-quantitative at sampling rates up to 32 L/min while the denuder shows <1% particle loss (for the particle size tested).

Other known wetted denuder systems operate vertically to avoid particle loss within in the denuder due to gravitational deposition. For example, Dasgupta et al. have described parallel plate wet denuders containing silica-coated wetted areas and a high flow (e.g., 50 L/min), and compact, multiple-parallel-plate denuder bearing eleven wetted polyester screens. See, e.g., Purnendu K. Dasgupta et al., *A Multiple Parallel Plate Wetted Screen Diffusion Denuder For High-Flow Air Sampling Applications*, Analytical Chemistry, vol. 69, no. 24, pp. 5018–5023 (1997). Jaeschke et al. have reported a tubular glass wet denuder in which the wetted denuder surface includes a nylon stocking material as the wall lining. See W. Jaeschke et al., *Phase Partitioning Of Ammonia And Ammonium In A Multiphase System Studied Using A New Vertical Wet Denuder Technique*, Atmospheric Environment, vol. 25, no. 3, p. 365–371 (1998). Recently, Rosman et al. presented a perfluoralkoxy (PFA) TEFLON, parallel-plate, wet denuder with a polyester lining for wettability. See Kai Rosman et al., *Laboratory And Field Investigations Of A New And Simple Design Of The Parallel Plate Denuder*, Atmospheric Environment, vol. 35, pp. 5301–5310 (2001). Such known wet denuders work well and are near-quantitative collectors of common soluble trace gases in the atmosphere at least up to sampling rates of 5 L/min.

A major shortcoming of known wetted denuders is that they must be operated strictly in the vertical orientation or the horizontal orientation for which they are designed. Any significant tilting, even for a limited time, can cause collector liquid to get into the air-sample inlet line causing subsequent analyte losses. For example, it would be of advantage to use wetted denuders during airborne sampling. Although an aircraft is usually on level flight during airborne sampling, the use of known wet denuders during aircraft-based airborne sampling is problematic. The aircraft may pitch, roll and/or yaw during a banked turn, while changing altitude, and/or when the aircraft subjected to turbulence, thus causing the denuder to tilt. In the event that one of the above wet denuders is used, analyte loss may occur when the collector liquid spills into and/or enters the air-sample inlet as the denuder is tilted.

In tubular-membrane-based denuders, often referred to as diffusion scrubbers, the sampled gas flows on one side of a membrane and the collector liquid flows on the other side. More commonly, hydrophobic membranes have been utilized in such tubular membrane-based denuders. Even when hydrophilic ion exchange membranes are used, for example, membranes of the type sold under the trademark NAFION sold by E. I. Du Pont De Nemours And Company of Wilmington, Del., the membrane thickness and water permeability through it are generally not high enough to keep the surface of the membrane that is in contact with the gas flow "wet". Moreover, ionogenic gases cannot be conveniently collected with ion exchange membranes as the analytes of interest are either too tightly bound to the membrane or they are Donnan-excluded. Recently introduced "artificial lung" samplers of the type described by Sakamoto et al. include a large number of hollow fibers, for example, approximately 10,000 polyolefin hollow fibers; these are likely to suffer from extensive particle deposition. See K. Sakamoto et al., *Development Of An Automatic Continuous Analyzer For Water-Soluble Gases In Air By Combining An Artificial Lung With An Ion Chromatograph*, Atmospheric Environment, vol. 36, pp. 441–448 (2002).

While there are advantages to known membrane based collectors, thus far, the maximum flow rate at which diffusion-scrubber based collectors can continuously remove atmospheric gases of interest has been quite modest and it would have been impractical to use them to remove gases ahead of a particle analysis system. In the recent past, particle analysis systems have typically relied on sampling rates of 4–5 L/min. Under these conditions, the ion chromatographic (IC) instrumentation used at the back end is sufficiently sensitive that the attainable limits of detection (LODs) were not only far below what was required for ambient air measurement, they were blank-variation limited. The present generation of IC instrumentation have become even more sensitive. With the current IC instrumentation, sampling rates of 1 L/min are sufficient to achieve low $ng/m^3$ LODs for most aerosol phase soluble ionic analytes of interest.

What is needed is a denuder for collection and removal of soluble atmospheric gases that overcomes the above and other disadvantages of known wet denuders and diffusion scrubbers.

BRIEF SUMMARY OF THE INVENTION

In summary, one aspect of the present invention is directed to a denuder for collection and removal of a gaseous analyte from a sample gas. The denuder includes a housing including an internal cavity, a sample gas inlet fluidly coupled with a sample gas source, a denuder liquid inlet fluidly coupled with a denuder liquid source, a barrier sheet extending across the internal cavity and separating the internal cavity into a liquid reservoir and a gas flow-through channel fluidly coupled with and downstream of the sample gas inlet, the barrier sheet having a liquid-reservoir surface and a gas-channel surface and being porous to gas and liquid; and a denuder liquid disposed in the liquid reservoir and permeating the barrier sheet to coat the gas-channel surface of the barrier sheet thereby allowing the denuder liquid on the gas-channel surface to contact the sample gas flowing within the gas flow-through channel and allowing the analyte to diffuse through the barrier sheet into the liquid reservoir.

The housing may be inert to the sample gas. Preferably, at least a portion of the housing is formed of polytetrafluoroethylene, perfluoroalkoxy polytetrafluoroethylene or polycarbonate.

Preferably, the barrier sheet is a membrane. The membrane may be hydrophilic. Suitably, the membrane may be formed of cellulose acetate, cellulose nitrate, other cellulose esters, NAFION, polyvinyl acetate or polysulfone. The barrier sheet may be substantially planar. The barrier sheet may be substantially vertically oriented or non-vertically oriented.

The side plate may have an internal recess defining a portion of the internal cavity. The liquid reservoir may be at least partially defined by the internal recess and the liquid-reservoir surface while the gas flow-through channel may be at least partially defined by the gas-channel surface the aperture of the spacer and the remaining portion of the internal cavity. In one embodiment, the side plate includes a textured surface within the internal recess.

In one embodiment, the side plate includes a denuder liquid inlet positioned at one end of the internal recess fluidly coupled to the denuder liquid reservoir and a denuder liquid outlet positioned at an opposing end of the internal recess. The denuder liquid outlet may be fluidly coupled with a detector for the analyte.

In one embodiment, the internal recess includes rectangular shape having V-shaped ends. The denuder liquid inlet may be positioned adjacent a lower one of the V-shaped ends and the denuder liquid outlet may be positioned adjacent an upper end of the V-shaped ends.

In one embodiment, the liquid reservoir includes a denuder liquid outlet fluidly coupled with a chromatography system. The chromatography system, especially an ion chromatography system, may include a fluorescence detector or an absorbance detector. The gas flow-through channel may include an outlet fluidly coupled with a particle detector, a particle collector or a particle analysis system.

In one embodiment, the housing includes a pair of parallel side plates, each side plate having an internal recess, a spacer disposed between the side plates and having a central aperture aligned with the internal recesses, the side plates and the spacer forming the housing wherein the central aperture and the internal recesses define the internal cavity, and a pair of barrier sheets separating the internal cavity into the gas flow-through channel and a pair of liquid reservoirs, each barrier sheet being disposed between the spacer and a respective one of the parallel side plates.

Another aspect of the present invention is directed to a method for collection and removal of at least one gaseous analyte in a sample gas, the method including the steps of providing a denuder having a barrier sheet extending across and separating an internal cavity in a housing into a gas flow-through channel and a liquid reservoir, providing a volume of denuder liquid in the liquid reservoir to permeate the barrier sheet and to coat a gas-channel surface of the barrier sheet with a film of the denuder liquid, flowing a sample gas through the gas flow-through channel whereby the film of the denuder liquid on the gas-channel surface contacts the sample gas flowing within the gas flow-through channel and the one analyte diffuses through the barrier sheet into the liquid reservoir, and removing the volume of denuder liquid, including the diffused one analyte, from the gas flow-though channel for analysis.

The one analyte may include an atmospheric gas soluble in aqueous liquid. In one embodiment, the method further includes the step of orienting the denuder such that the barrier sheet may be vertically oriented. Alternatively, method may include the step of orienting the denuder such that the barrier sheet may be non-vertically oriented.

In one embodiment, the denuder includes a pair of parallel side plates, each having an internal recess partially defining a respective liquid reservoir, and a spacer having a central aperture aligned with the internal recesses and partially defining the gas flow-through channel, in which case, the method further includes the steps of disposing a barrier sheet between the spacer and each one of the parallel side plates to separate the internal cavity into the gas flow-through channel and a pair of liquid reservoirs, and securing the spacer and the parallel side plates together.

The method may further include the step of trimming the barrier sheets along at least one of an outer periphery of the parallel side plates and an outer periphery of the spacer. The method may include detecting the diffused analyte in the removed denuder liquid.

In one embodiment, the sample gas includes at least a second analyte and the method further includes the step of separating the one and separate second analyte prior to detection. The separation may be performed by chromatography, especially ion chromatography, fluorescence detection or absorbance detection.

In one embodiment, the sample gas further includes particles and the method further includes analyzing the particles in the sample gas after they exit from the gas flow-through channel largely not removed.

An object of the present invention is to provide a continuously wetted denuder assembly that can be readily coupled with an analysis system, for example, an ion chromatography system, and which enables simultaneous near real-time measurement of one or more sample gases.

Another object of the present invention is to provide a method of using the above continuously wetted denuder assembly that enables simultaneous near real-time measurement of several gases.

It is a further object of the present invention to provide a continuously wetted denuder assembly having a membrane-contained liquid flow path that minimizes and/or prevents spillage of a denuder liquid into inlet lines regardless of the angular inclination of the denuder assembly.

The denuder assembly for collection and removal of soluble atmospheric gases of the present invention has other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

FIG. 1 is a side elevational view of a denuder assembly for the collection and removal of soluble atmospheric gases in accordance with the present invention. The denuder assembly includes a pair of membranes disposed between a spacer and respective side plates.

FIG. 2 is a front elevational view of one of the side plates of FIG. 1.

FIG. 3 is a front elevational view of the spacer of view of FIG. 1.

FIG. 4 is an enlarged detailed view of the denuder assembly of FIG. 1.

FIG. 5 is a schematic view of a system configured for the measurement of gas collection efficiency, which system incorporates the denuder assembly of FIG. 1.

FIG. 6 is a schematic view of a system configured for the measurement of particle loss, which system incorporates the denuder assembly of FIG. 1.

FIG. 7 is a schematic view of a system configured for the measurement of particle loss similar to that of FIG. 6, but shown with the denuder assembly of FIG. 1 horizontally oriented.

FIG. 8 is a schematic view of a system configured for the measurement of residence volume, which system incorporates the denuder assembly of FIG. 1.

FIG. 9 is a graph illustrating gas collection efficiency as a function of sampling rate and denuder liquid composition in accordance with the present invention.

FIG. 10 is a schematic view of a system for the collection and removal of soluble atmospheric gases in accordance with the present invention incorporating the denuder assembly of FIG. 1.

FIG. 11 a schematic view of an alternative system for the collection and removal of soluble atmospheric gases in accordance with the present invention incorporating the denuder assembly of FIG. 1.

FIG. 12 is a front elevational view of a modified spacer similar to that shown in FIG. 3.

FIG. 13 is a front elevational view of one of a modified side plates similar to that shown in FIG. 2.

FIG. 14 is an exploded, side elevational view of the spacer of FIG. 12 and the end plate of FIG. 13, take along lines 14a–14a and 14b–14b of FIG. 12 and FIG. 13, respectively.

DETAILED DESCRIPTION OF THE INVENTION

Reference is made in detail to the preferred embodiments of the invention, examples of which are illustrated in the accompanying drawings. While the invention is described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Turning now to the drawings, wherein like components are designated by like reference numerals throughout the various figures, attention is directed to FIG. 1, which figure schematically illustrates one embodiment of a denuder assembly, generally designated by the numeral 30, for the collection and removal of a gaseous analyte from a sample gas in accordance with the present invention. The denuder assembly is configured for the collection and removal of atmospheric trace gases and may be incorporated in various analytical systems including, but not limited to, chromatography systems and extraction systems, which systems are configured to separate, isolate, and identify the components of chemical mixtures in the environmental, pharmaceutical, life science, biotechnology, chemical, petrochemical, power generation and electronics industries.

Generally, denuder assembly 30 includes a housing 31 having an internal cavity 32 and a pair of barrier sheets 33. The barrier sheets extend across the internal cavity and separate the cavity into a corresponding pair of liquid reservoirs 34 and a gas flow-through channel or gas channel 35. Gas channel 35 is fluidly coupled with a sample gas source such that a sample gas will flow through the gas channel. Each liquid reservoir 34 is configured to receive and hold a volume of sample collecting liquid or denuder liquid 36 such that the denuder liquid to permeates barrier sheet 33 and forms a film 37 on the barrier sheet that provides direct gas/liquid contact between the sample polyolefins, gas and the denuder liquid, as best seen in FIG. 4.

The barrier sheet configuration of the denuder assembly provides a denuder assembly having direct gas/liquid contact and which can tolerate any angular inclination without leakage of the denuder liquid in to a sample gas inlet of the gas channel. Thus, the denuder assembly of the present invention minimizes and/or prevents the possibility of liquid leakage into the air sampling inlet and thus promotes accurate analysis of the sample gas.

In one embodiment, housing 31 includes a pair of substantially parallel end plates 38 and a substantially flat spacer 39 disposed between the end plates, as shown in FIG. 1. Preferably, the housing is formed of a material that is inert to the sample gas. For example, the housing may be formed of a polymeric material including, but not limited to, polytetrafluoroethylene, perfluoroalkoxy polytetrafluoroethylene (e.g., PFA TEFLON), and/or polycarbonate. One will appreciate that the housing may be formed of other suitable materials that provide sufficient structural integrity and are substantially inert to the intended sample gases.

Each side plate has an internal recess 40 while the spacer has a central aperture 41 aligned with the internal recesses of the side plates. Together, the internal recesses of the side plates and the aperture of the spacer form the internal cavity 32 of housing 31. One will appreciate that the housing may have other configurations. For example, the spacer and one end plate may be replaced a single unitary block having a recessed channel, in which case a single end plate caps off the recessed channel. Also, one, two, three or more spacers may be provided to separate the internal cavity into a plurality of sample gas channels and/or liquid reservoirs, as will become apparent below.

In the illustrated embodiment, the internal recess of each end plate has a rectangular shape and V-shaped ends 42, 43, as shown in FIG. 2. Preferably, a denuder liquid inlet 44, which is fluidly connected to a denuder liquid supply 45 (see, e.g., FIG. 5), is positioned adjacent the lower V-shaped end 43. This low-inlet configuration lessens the head pressure of the volume of denuder liquid within the liquid reservoir and thus minimizes and/or prevents the denuder liquid from causing the barrier sheet from bowing, bulging and/or flexing inwardly, namely due to positive hydrostatic pressure. A denuder liquid outlet 46, which is fluidly connected to chromatography or other analysis system, is positioned adjacent the upper V-shaped end 42. One will appreciate, however, that a denuder liquid outlet need not be provided, in which case, the denuder liquid circuit may be configured to remove the volume of denuder liquid from the liquid reservoir via the liquid inlet.

In the embodiment illustrated in FIG. 2, internal recess 40 of each end plate comprises an approximately 100 μm deep channel starting approximately 40 mm from both the upper and lower ends of the end plate. In this embodiment, the internal recess is approximately 220 mm long and approximately 13 mm wide. The surface of the channel is machined to improve wettability, that is, machined to provide a textured surface finish promoting retention of denuder liquid on the surface of the internal recess to facilitate the denuder liquid in filling the liquid reservoir. A wettable texture may be formed by machining fine grooves on the surface in a crosshatch pattern that forms a diamond pattern or "knurl" which is not conducive to a linear flow of liquid. In addition to the pattern of small diamonds, the surface finish may be left rough, e.g., with the tool marks from machining are left in place, to facilitate dispersion of the denuder liquid over a wider area.

In one embodiment, the spacer includes a pair of identical halves that are machined from substantially flat PFA TEFLON plates. One will appreciate, however, that the spacer halves may be formed of other suitable materials, as noted above with reference to housing 31. Preferably, the spacer halves are approximately 2.0 mm thick. Upper and lower ends 47, 48 of the spacer contain grooves 49, 50 for receiving suitable tubing through which the sample gas flows from a sample gas supply, into and out from the gas flow-through channel. For example, grooves 49, 50 may be dimensioned and configured to receive a 0.25 in. o.d. PFA TEFLON tubing, or other suitable fluid circuit means, fluidly connecting denuder assembly 30 with an upstream sample gas supply 51 (see, e.g., FIG. 5) and a downstream analytical device (see, e.g., filter 67, FIG. 6) and/or an exhaust or vent to atmosphere.

Preferably, spacer 39 and end plates 38 are readily assembled and disassembled using suitable fastening means including, but not limited to, screws, nuts and bolts, and/or other well-known fastening means. In the embodiment illustrated in FIG. 1, the housing includes twenty-eight screw holes on each end plate and spacer. The holes in one end plate are threaded holes 52 provided with 8–32 threads. The other end plate and the spacer contains pass-through holes 53. Thus, one may readily assemble, disassemble and reassemble the housing as desired simply by screwing the assembly together using a plurality of assembly screws 54.

Turning now to the barrier sheets, barrier sheets 33 extend across internal cavity 32 and separate the internal cavity into gas flow-through channel 35 and a pair of denuder liquid reservoirs 34. Each barrier sheet has a liquid-reservoir surface 55 and a gas-channel surface 56, as shown in FIG. 4. Each liquid reservoir 34 is a predetermined volume defined by the internal surface of a respective internal recess 40 and liquid-reservoir surface 55 of the barrier sheet. The remainder of the internal cavity of housing 31 forms the gas flow-through channel. Gas channel 35 is a predetermined volume defined by the interior surface of spacer 39 and the gas-channel surfaces 56 of the substantially parallel, spaced-apart barrier sheets.

The configuration of the barrier sheet provides a membrane-contained flow path of the denuder liquid. The rate of liquid penetration through the barrier sheet is low enough that under use conditions, barrier sheet 33 substantially contains denuder liquid 36 within liquid reservoir 34, with the exception of thin film 37, and thus prevents bulk liquid leakage into gas channel 35. Thus, spillage of the denuder liquid into gas channel is prevented regardless of the angular inclination of denuder assembly 30.

Thus, the barrier sheet configuration prevents spillage of denuder liquid 36 into the gas inlet and/or outlet lines (e.g., grooves 49, 50), even if denuder assembly 30 is tilted away from a vertical orientation. One will appreciate that avoiding such spillage into the inlet line will prevent loss of soluble gases before the gas stream enters the denuder assembly.

Barrier sheets 33 are permeable to gas and liquid and thus facilitate the diffusion of a sample gas analyte through the barrier sheets and into the liquid reservoirs. Thin liquid film 37 on gas-channel surface 56 of the barrier sheet serves as a sample-gas-analyte sink. Once the sample gas analyte is collected by or diffused into the liquid film, the sample gas analyte is in a condensed phase, that is, no longer in the gas phase. The condensed phase of the sample gas analyte permeates the membrane in the form of a solution phase analyte. In the illustrated embodiment, the barrier sheets are substantially planar and are substantially vertically oriented. One will appreciate, however, that the configuration of each barrier sheet may vary. For example, the general shape of at least one of the barrier sheets may be flat, creased, arcuate and/or corrugated. Also, at least one of the barrier sheets may be non-vertically oriented. For example, one or more of the barrier sheets may be horizontally oriented or oriented at an inclined angle.

Although the embodiment illustrated in FIG. 1 includes a pair of barrier sheets, one will appreciate that the denuder assembly of the present invention may include one, two, three or more barrier sheets which separate the internal cavity into one or more gas flow-through channels and one or more liquid reservoirs. For example, the internal cavity of the denuder assembly may be separated into a plurality of gas flow through channels, each having one or more dedicated denuder liquid reservoirs thus providing a multichannel denuder assembly.

Preferably, the barrier sheets are hydrophilic membranes and formed of a material that is porous to gas and liquid. Suitable materials for the barrier sheets include, but are not limited to, cellulose acetate, cellulose nitrate, other cellulose esters, NAFION, polyvinyl acetate, polysulfone and/or other suitable materials. In the illustrated embodiment, each barrier sheet is a regenerated cellulose dialysis membrane of the type sold by Membrane Filtration Products, Inc. of Seguin, Tex. under the trademark CELLU-SEP. For example, one suitable membrane is the CELLU-SEP T3, Type 1210-100 membrane, which membrane has a molecular weight cut-off of approximately 12,000–14,000, is sold in tubular form having a flat width of approximately 100 mm, and has a "wet" thickness, that is, the thickness of the membrane sheet when water-saturated, of approximately 107 μm. The tubular CELLU-SEP T3 membrane is slit open to form a single layer barrier sheet having a width of approximately 200 mm.

Preferably, the barrier sheet is formed of a wettable membrane of sufficient thinness through which water, or other denuder liquid, permeates the membrane sufficiently to wet the opposite side (e.g., to form film 37 on gas-channel surface 56) but is substantially non-flowing through the membrane, that is, the liquid does not permeate the membrane to the degree that allows water to accumulate and substantially drip from, or cascade down, the opposite side of the membrane. Also, preferably, the membrane is not so thick as to hinder or delay the transport of collected analyte through the membrane to the liquid side of the membrane but is thick enough to maintain structural integrity. The permeability of barrier sheet 33 allows film 37 to substantially cover the entire gas-channel surface 56 and serve as a sink for the sample gas analyte. Such a configuration is significantly more efficient than prior hydrophobic-membrane configurations as the contact area between the sample gas and the denuder liquid is significantly increased.

Denuder assembly 30 is readily assembled by placing a first barrier sheet 33 between spacer 39 and one of the end plates 38 and placing a second barrier sheet between the spacer and the other of the end plates. As the membranes utilized for the barrier sheets often dimensionally change upon wetting, the barrier sheets are preferably wetted prior to assembly in order to accommodate such dimensional changes. Doing so minimizes bulging of the barrier sheet as the liquid reservoir is filled with the denuder liquid. With the wet membrane sheets 33 and spacer 39 in place between the end plates 38, assembly screws may be inserted into their respective screw-hole and tightened thereby securing the spacer and endplates together thereby assembling the housing. As the width of the barrier sheet is generally oversized, that is, the barrier sheet is wider than the spacer and the end plates, any excess membrane is trimmed off after the housing is assembled.

One will appreciate that the effective separation between the two active collection surfaces, that is, the effective separation between gas-channel surfaces 56 of the substantially parallel barrier sheets is the thickness of spacer 39. One will appreciate that the effective separation may be varied by replacing the spacer with one or more spacers to attain the desired thickness.

Once the denuder assembly is assembled, denuder liquid outlet 46 can be fluidly coupled with a detector for analyzing the denuder liquid containing the analyte removed from the sample gas in a well-known manner. For example, denuder liquid outlet 46 can be fluidly coupled with fluid-analysis equipment, indicated generally by the numeral 57. The fluid-analysis equipment may be a chromatography system, including, but not limited to, an ion chromatography system. The detector may be any type used for chromatography applications, including a conductivity detector, a fluorescence detector, or an absorbance detector. One will also appreciate that the gas outlet of gas flow-through channel 35 maybe fluidly coupled with gas-analysis equipment in a well-known manner. The gas-analysis equipment, indicated generally by the numeral 58 may include, but is not limited to, particle detectors, particle collectors and/or particle analysis systems. Alternatively, in the event that further analysis of the sample gas is not desired, the gas outlet of the gas flow-through channel may simply be vented to atmosphere.

In one embodiment, collecting or denuder liquid 36 substantially fills liquid reservoir 34, preferably to a level that the liquid contacts the length of the exposed barrier sheet. The denuder liquid in the liquid reservoir permeates barrier sheet 33 and coats gas-channel surface 56 of the barrier sheet. The permeated-sheet configuration provides a thin film 37 of denuder liquid on the gas-channel surface which is in direct gas-liquid contact with any sample gas flowing within gas flow-through channel 35. The permeated-sheet configuration allows the analyte from the sample gas to diffuse through barrier sheet 33 into and into the volume of denuder liquid 36 filling liquid reservoir 34.

A method of collection and removal of at least one gaseous analyte in a sample gas can now be described. As noted above, denuder assembly 30 includes a pair of barrier sheets 33 which extend across and separate an internal cavity 32 of housing 31 into a gas flow-through channel 35 and a pair of liquid reservoirs 34. A predetermined volume of denuder liquid 36 is provided in the liquid reservoirs, which liquid permeates the barrier sheet and coats gas-channel surfaces 56 of the barrier sheets with a film 37 of the denuder liquid.

A sample gas that is to be analyzed, and which is generally an atmospheric gas soluble in aqueous solution, is directed to flow through gas channel 35. As the sample gas passes through the gas channel, the sample gas is in direct contact with a film 37 of the denuder liquid on gas-channel surfaces 56 of the barrier sheets. Analyte from the sample gas diffuses into and is retained by the denuder liquid, through barrier sheets 33, and into liquid reservoirs 34. In one embodiment, the sample gas dissolves in the denuder liquid.

Once a predetermined interval of time passes, a volume of denuder liquid, which includes the diffused analyte, is removed from liquid reservoirs 34 and, preferably, directed to fluid analysis equipment 57 for analysis, as shown in FIG. 10.

One will appreciate that various denuder liquids may be used to capture different analytes from the sample gas. In the event that one wishes to perform determination of multiple analytes in the sample gas, the method may further include the step of removing a second, third, etc. analyte from the sample gas and separating the said analytes in the denuder liquid(s), prior to detection. Such a separation may be performed by chromatography. The separation may be performed by various processes including, but not limited to, chromatography of various forms including ion chromatography, followed by detection as by conductivity, fluorescence, absorbance, and/or other detection modes well known in the field.

Generally, analyte gases of interest may be captured by the denuder liquid from the sample gas merely by dissolution (e.g., gases like $H_2O_2$ have extremely high solubility for example; similarly formaldehyde also dissolves in water as methylene glycol). The capture may be aided by including a component in a denuder liquid which reacts with and thereby retains the sample gas. For example, the uptake of formaldehyde can be enhanced by adding bisulfite to the collection or denuder liquid so that the aldehyde-bisulfite adduct is formed. The uptake of acidic gases can be enhanced by adding a base to the denuder liquid to form a salt and the uptake of basic gases can be aided by adding acid to form a salt. For example, the uptake of ammonia can be enhanced by adding dilute $H_2SO_4$ to the denuder liquid. One will appreciate that there can be other types of reactive uptake. For example, the addition of $H_2O_2$ to the denuder liquid enhances for example the uptake of $SO_2$ by forming $H_2SO_4$, and this can be further enhanced by further adding NaOH to make the solution alkaline. In the event that the barrier sheet is formed of an ion exchange membrane, for an aqueous denuder liquid, the barrier sheet may provide a hydrated ion exchange site that produces a pool of water which forms a continuous liquid path through the membrane.

Once analyte gases, normally soluble gases, are removed by the denuder liquid, soluble constituents of particles can be readily analyzed by scrubbing them into a solution and sending the resulting solution containing dissolved particle constituents for analysis, e.g., by ion chromatography, see, e.g., P. K. Simon et al. *Continuous Automated Measurement of the Soluble Fraction of Atmospheric Particulate Matter*, Analytical Chemistry, vol. 67, pp. 71–78 (1995); P. K. Simon et al., *Continuous Automated Measurement of Gaseous Nitrous and Nitric Acids and Particulate Nitrite and*

*Nitrate*, Environmental Science & Technology, vol. 29, pp. 1534–1541 (1995); C. B. Boring et al., *Field Measurement of Acid Gases and Soluble Anions in Atmospheric Particulate Matter using a Parallel Plate Wet Denuder and an Alternating Filter-Based Automated Analysis System*, Analytical Chemistry, vol. 74, pp. 1256–1268 (2002), the entire content of which is incorporated herein by this reference.

EXAMPLES

Unless otherwise stated in the following experiments, the following test denuder assemblies were operated in a vertical configuration and the denuder liquid was aspirated from a reservoir placed immediately below the level of the denuder assembly.

Gas Generation and Collection Efficiency Measurement

With reference to FIG. 5, the gas collection efficiency of a test denuder assembly 30 was measured with sulfur dioxide ($SO_2$) gas which was generated using Henry's law based porous membrane sources immersed in a solution containing known concentrations of aqueous bisulfite solution buffered at pH 4. The 1.0 ppmv $SO_2$ test stream was brought into the test denuder assembly over a flow rate range of 1.0–2.0 standard liters per minute (SLPM). A 60 cm long expanded PTFE membrane tube diffusion scrubber (ePTFE MDS), generally designated by the numeral 59, followed test denuder assembly 30 in series. The general arrangement is shown in FIG. 5. For test denuder assembly 30, 5 mM $H_2O_2$ or 5 mM $H_2O_2$+5 mM NaOH solutions was used for the denuder liquid. For the diffusion scrubber, 5 mM $H_2O_2$ was used as the scrubber or denuder liquid. Both the denuder liquid and the scrubber liquid flowed at 500 µL/min, aspirated by a GILSON Minipuls 2 peristaltic pump 60 (sold by Gilson, Inc. of Middleton, Wis.). The conductivity signal ($S_1$) of the ePTFE diffusion scrubber effluent was measured with a CDM-2 conductivity detector 61 (sold by Dionex Corporation of Sunnyvale, Calif.). The conductivity signal was also measured without the test denuder assembly in place ($S_2$). The fractional collection efficiency f was calculated as follows:

$$f = (1 - S_1 S_2) \qquad \text{Equation (1)}$$

Particle Generation and Particle Loss Measurement

Particle generation and particle loss of a test denuder assembly 30 was measured. The general experimental setup appears in FIG. 6. A vibrating orifice aerosol generator 62 (Model 3450, sold by TSI, Inc. of St. Paul, Minn.) was used to generate monodisperse NaCl aerosols doped with fluorescein, so that the aerosols could be easily measured. If a pure compound is nebulized from a droplet based aerosol generator, the eventual dry particle size is proportional to the cube root of the feed solution concentration. Sodium chloride solutions, 5 µM, 50 µM, 500 µM, 2.5 mM, and 5.0 mM in concentration, were respectively used for particle generation. All NaCl solutions were doped with fluorescein as a tracer. Nominally, these generated particles were 0.24 µm, 0.52 µm, 1.1 µm, 1.9 µm and 2.4 µm in diameter, respectively.

The aerosol generator was operated with a 20 µm diameter orifice, 60 mL syringe capacity, syringe pump speed of $5.0 \times 10^{-4}$ cm/s (flow rate 0.165 cm³/min), drive frequency 50.5 kHz, primary airflow of 1.5 SLPM and dilution air flow of 35.0 SLPM. Aerosol free 'zero' air was generated by a pure air generator 63 (AADCO Model 737-14, sold by the Advanced Analytical Device Company of Cleves, Ohio) having a capacity of 100 SLPM. The primary aerosol generated was diluted and dried with the secondary airflow. The aerosol then passed through the Kr-85 neutralizer 64 (Model 3054 Aerosol Neutralizer, sold by TSI, Inc. of St. Paul, Minn.) to allow the aerosol to attain equilibrium Boltzmann Charge. The aerosol stream was then put through two sequential 20-L volume polyethylene chambers for drying to be completed. Using splitters 65, the flow was divided into three streams. One stream was sampled by a laser-based multichannel (six ranges, 0.1 to >3.0 µm) optical particle counter 66 (Model A2212-01-115-1, sold by Met-One of Grant's Pass, Oreg.) in order to measure the aerosol size distribution. The test denuder assembly 30 (operated in vertical configuration, e.g., FIG. 6, or horizontal configuration, e.g., FIG. 7) was followed by a filter 67 (47 mm diameter glass fiber filter, WHATMAN type GF/A, manufactured by Whatman International Ltd. of Maidstone, Kent, UK), connected to its own aspiration pump (AP) 68 and mass flow controller (MFC) 69, sampled the second stream. The third stream vented the excess flow from the aerosol source.

Sampling through the denuder-filter assembly was conducted for 1–2 hours at an air flow rate of 1.0 or 2.0 SLPM. The filter was ultrasonically extracted for 10 min in to 20 mL water and syringe filtered (0.2 µm) prior to fluorescence measurement. The denuder effluent liquid (pure water was used as the input liquid for denuder aerosol deposition measurements at a flow rate of 500 µL/min) from the test denuder assembly was also collected and its fluorescence measured. Any soluble aerosol that deposits on the wet membrane is dissolved and incorporated into the denuder effluent liquid. The extent of aerosol deposition on the air inlet and outlet tubes (0.16 in. i.d. ×0.25 in. o.d.×50 mm long) of the test denuder assembly was also measured by post-sampling extraction of these sections with 10 mL of pure water. All of the water extracts were subjected to fluorescence measurement after 1 drop of 2 N NaOH was added to each extract, using $\lambda_{ex}$=490 nm and $\lambda_{em}$=520 nm (model RF-540 spectrofluorometer, Shimadzu). The total particle loss (TPL) in the test denuder assembly was calculated as follows:

$$TPL = (a+b)/(a+b+c) \times 100\% \qquad \text{Equation (2)}$$

where a, b, and c are respectively the total mass of fluorescein found in (a) the denuder liquid effluent, (b) the denuder air inlet/outlet tubes and (c) the backup filter extract.

Liquid Residence Volume

The liquid residence volume of a test denuder assembly 30 was measured with the denuder liquid reservoir 45 placed immediately (a) above and (b) below the test denuder assembly. Because the membrane is thin and flexible, the membrane may bulge under positive hydrostatic pressure. The test arrangement is shown in FIG. 8. The liquid residence volume was measured with a total liquid flow rate of 480 µL/min and an air sampling rate of 1.2 SLPM. An injection of 100 µL of 5 mM NaCl was made with a loop injector. The time for the appearance of the peak from the moment of injection was measured (t). The time for a corresponding blank (all components in place except the denuder assembly is omitted and the tubes normally connected to it are directly connected to each other ($t_0$). The corrected time (t-$t_0$) multiplied by the liquid flow rate then yielded the mean residence volume.

Response Time to an Analyte Gas.

The speed with which the denuder assembly responds to a momentary pulse in the test gas concentration was measured by the 10–90% rise time and 90–10% fall time in the conductivity signal as pulses of 1 ppmv $SO_2$, was applied to the test denuder assembly at a gas flow rate of 1 SLPM with 5 mM $H_2O_2$ flowing through the denuder assembly at 500 μL/min. These experiments were conducted both with test gas pulse durations that are short (1 min) or long (10 min) relative to the observed response time of the device with both co-current and countercurrent gas-liquid flow.

Gas Removal Efficiency of the Denuder Assembly

Assuming that the plates are perfect sinks for a gas under laminar flow condition, the ideal collection efficiency f of a parallel plate denuder assembly having two identical plates, for a gas of diffusion coefficient D ($cm^2/s$) flowing at a volumetric flow rate of Q ($cm^3/s$), is given by:

$$f=1-0.91 \exp(-2.4 \pi wDL/Qs) \quad \text{Equation (3)}$$

wherein each parallel plate has a length L (cm) and a width w (cm) in active area, and wherein the parallel plates are separated by a distance s (cm).

Since Lw only occurs as a product in the above equation, the aspect ratio is not important, it is only the total area that is important. Equation (3) predicts idealized (maximum possible) collection efficiency because it assumes that every collision of a gas molecule with the active collection surface results in uptake of the gas molecule. For a highly soluble gas and a wet surface, this is nearly attained. The ideal and experimental collection efficiencies of the test denuder assembly are shown in FIG. 9 for 1 ppmv $SO_2$ gas. The hollow and solid circles show the collection efficiencies using 5 mM $H_2O_2$ and 5 mM $H_2O_2$+5 mM NaOH solutions as a denuder liquid, respectively. The solid lines are the best fit of experimental results for each denuder liquid, while the dashed line shows the ideal collection efficiency (L=22 cm, w=1.3 cm, s=0.2 cm, the best estimate for D for $SO_2$ at 296 K is 0.12 $cm^2/s$, in good agreement with the earlier measurement of Fish and Durham).

The above results show that the collection efficiencies follow ideal behavior and are nearly quantitative up to a sampling rate of 28 $cm^3/s$ (1.4 SLPM, ambient pressure and temperature 680 mm Hg, 296 K). At higher flow rates, the experimental collection efficiencies are less than the ideal calculated values. The efficiency of the membrane surface as a sink obviously depends on the NaOH and/or $H_2O_2$ incorporated in the denuder liquid; indeed the NaOH+$H_2O_2$ composition is discernibly better than $H_2O_2$ alone. This suggests that surface saturation may be occurring at the higher flow rates. This also suggests that theoretical collection efficiencies will likely persist beyond what is observed here at lower test $SO_2$ concentrations or higher concentration of sink reagents. Similarly, theoretical collection efficiencies are expected to persist beyond a sampling rate of ~30 $cm^3/s$ for nitric acid ($HNO_3$), a gas with similar diffusion coefficient as $SO_2$ but a much greater sticking coefficient. It is also important to note that it is not the mass flow rate of the gas but its velocity through the denuder assembly that is relevant in determining the collection efficiency.

In the above experiments it a 99+% collection efficiency for $SO_2$ was observed (and theoretically predicted) at flow rates of 1.4 standard liters/min (SLPM). the experimental laboratory was at an altitude of 988 m. At sea level, greater mass flow rates than 1.4 SLPM will be possible while still attaining theoretical collection efficiency. At higher altitudes/lower ambient pressures, the maximum permissible mass flow rate must be decreased if near-quantitative collection efficiency must be maintained. The present membrane denuder assembly should clearly be able to attain near-quantitative collection efficiencies for the most important inorganic atmospheric gases HCl, HONO, $HNO_3$, $SO_2$ and $NH_3$ at a flow rate of 1 SLPM down to pressures of 485 mm Hg (nominally up to an altitude of 11900 ft/3600 m).

Equation (3) predicts a linear relationship between ln(1−f) and the reciprocal of the sampling rate. For both absorbers used here, linear $r^2$ values for this relationship were ≧0.99.

Particle Loss

Table I shows the particle loss in the test denuder assembly. When operated in the vertical configuration, the particle loss in the test denuder assembly ranged from 0.88% to 2.88% and averaged 1.79% over a particle aerodynamic diameter range of 0.38 to 3.48 μm and at an air flow rate of 1.0 and 2.0 SLPM. Only ~0.5% of the particles actually appeared in the denuder liquid. The particle loss for the smaller submicron particles was higher at the lower air flow rate and mostly took place in the inlet/outlet TEFLON tubes, probably mostly due to electrostatic reasons and greater diffusivity of the small particles. The horizontal configuration leads to much greater loss, especially for the larger particles presumably due to gravitational settling. For the 1.93 μm test particles, for example, the loss exceeds 10%. Therefore, this configuration is not recommended and extensive further tests were not conducted.

TABLE 1

Particle Loss Data

| Spherical Equivalent Diameter | Aerodynamic Diameter* | Percent Particle Loss | | | | | |
|---|---|---|---|---|---|---|---|
| | | Inlet/Exit Tubes | | Denuder Liquid | | Complete Denuder | |
| μm | μm | 1 SLPM | 2 SLPM | 1 SLPM | 2 SLPM | 1 SLPM | 2 SLPM |
| 0.24 | 0.38 | 1.48 | 1.55 | 0.07 | 0.01 | 1.54 | 1.56 |
| 0.52 | 0.77 | 0.86 | 1.91 | 0.02 | 0.07 | 0.88 | 1.98 |
| 1.13 | 1.64 | 1.09 | 2.02 | 0.02 | 0.01 | 1.11 | 2.03 |
| 1.93 | 2.77 | 2.1 | 2.65 | 0.5 | 0.23 | 2.60 | 2.88 |
| 2.43 | 3.48 | 1.05 | 1.86 | 0.22 | 0.19 | 1.27 | 2.06 |
| Mean. | | 1.32 | 2 | 0.16 | 0.1 | 1.48 | 2.10 |

*Assumes unit density, takes into account cubic shape of sodium chloride (NaCl) particles and applies Cunningham slip correction.

Liquid Residence Volume

The liquid residence volume (LRV) of the test denuder assembly was measured to be 690 μL (±0.74% in relative standard deviation, n=3) with the water reservoir placed immediately below the level of the denuder assembly. This did not change significantly whether or not air was sampled through the denuder assembly. However, if the position of the reservoir was raised just above the denuder assembly, the outward pressure on the liquid side of the membrane was much greater and the LRV more than doubled to 1.88 mL (±1.6%, n=3). Note that all performance specifications are affected by the hydraulic pressure exerted by the liquid reservoir. If hydraulic pressure causes the membranes to bulge out, the particles deposit more readily on the protruding membranes (conversely a decrease in the intermembrane separation s increases gas collection efficiency. In our application, a large increase in particle deposition is not acceptable and as such we have always operated without significant hydrostatic pressure on the membranes.

The residence volume of each individual plate was also determined. In repeated determinations and upon repeated assembly, the individual plate volumes were not identical but the variation was typically less than 5% from one side to the other and between different trial assemblies.

Response Time

The rate at which the analyte ions/molecules derived from the target gases of interest pass through the membrane and appear in the detector stream is ultimately the factor that determines how fast the overall analytical system will respond to changing gaseous analyte concentrations if analysis or analytical reaction times are not the rate determining steps. Although wet denuders have generally been used with ion chromatography (IC) systems where IC cycle times for each chromatogram (of the order of 5–15 min) becomes the determining factor, there are other nonionic polar analytes such as formaldehyde (HCHO) and peroxides where fast analytical reactions are used where the membrane response can become the limiting factor. In general, these instruments operate on a short sampling and long zero duration (e.g., 2 min sample 8 min zero). We therefore determined the response time both for a sample pulse of short (1 min) duration and the same duration (15 min) that we are currently using with our IC instruments. The results are shown in Table 2.

TABLE 2

Response Time*

|  | Rise time (10–90%) min, (% RSD, n > 3) | Fall time (90–10%) min, (% RSD, n > 3) |
|---|---|---|
| A. Sample Pulse Duration 1 min | | |
| Co-Current Flow | | |
| Both Plates with Liquid flow | 2.08 (4.0) | 3.61 (1.3) |
| Plate A only with Flow | 1.19 (4.0) | 2.56 (1.9) |
| Plate B only with Flow | 1.36 (3.5) | 2.61 (1.8) |
| Countercurrent Flow | | |
| Both Plates with Liquid flow | 1.17 (0.0) | 3.58 (4.0) |
| Plate A only with Flow | 0.94 (5.1) | 2.53 (1.9) |
| Plate B only with Flow | 0.94 (5.1) | 2.69 (4.7) |
| B. Sample Pulse Duration 15 min | | |
| Co-Current Flow | | |
| Both Plates with Liquid flow | 4.58 (1.8) | 4.92 (2.9) |
| Plate A only with Flow | 3.00 (5.6) | 3.08 (0.0) |
| Plate B only with Flow | 2.92 (0.0) | 3.00 (0.0) |
| Countercurrent Flow | | |
| Both Plates with Liquid flow | 3.86 (2.5) | 4.30 (2.2) |
| Plate A only with Flow | 2.64 (1.8) | 2.75 (3.0) |
| Plate B only with Flow | 2.64 (1.8) | 2.86 (1.7) |

*Air flow rate 1 SLPM; total liquid flow rate (one or both plates active) 500 µl/min.

The two different sampling situations describe (a) a transient situation and (b) a steady state situation; in the later case, complete equilibration is achieved between the sampled gas and the denuder liquid effluent. For following fast changes in the sample concentration, it is really situation a that is more relevant. It will be noted that countercurrent operation always produces substantially better rise times, while fall times, which are likely limited by the diffusion times through the membrane, are essentially the same for co-current or countercurrent flow. As with the comparability of the LRV values for each plate, operating each plate independently gives essentially the same results while the response time from the two plates together produces a value close to the expected root mean square sum of the two individual plate response times.

In summary, we have described here a membrane-based denuder assembly of a convenient size that can quantitatively remove common atmospheric acidic and basic gases at a flow rate of at least approximately 1 L/min and demonstrably exhibits very low particle deposition. The denuder assembly of the present invention may be used in combination with a complete system having a matching particle collector. It may be possible to use a zwitterionic buffer in such a denuder assembly to collect and ion-chromatographically analyze both acidic and basic gases in independent IC systems, and it may be possible to operate each plate with independent liquids.

Advantageously, the denuder assembly of the present invention can remove soluble atmospheric gases such as, but not limited to, $SO_2$ essentially quantitatively at flow rates of in excess of 1 L/min.

In one embodiment of the present invention, a system 70 incorporating denuder assembly 30 is configured to simultaneously capture two analytes from the sample gas, as shown in FIG. 11. Like reference numerals have been used to describe like components. The gas channel of the denuder assembly 30 is fluidly connected with a sample gas supply 51 and gas analysis equipment 58 in manner similar to that described above. In this embodiment, however, each liquid reservoir 34, 34' has a dedicated liquid supply 45, 45', in which one denuder liquid, particularly suited for one type of analyte, is supplied to the left reservoir 34 while a second denuder liquid, particularly suited for another type of analyte, is supplied to the right reservoir 34'. The left and right reservoirs, in turn, are fluidly coupled to discrete fluid analysis devices 57, 57' in order to allow separate analysis of two different analytes taken from the same gas sample.

In another embodiment of the present invention, the denuder assembly includes a modified spacer/end plate configuration, as shown in FIG. 12 through FIG. 14. In this embodiment, the end plate 38a has a raised step or shoulder portion 71 which has a peripheral shape that is complimentary to the shape of central aperture 41a of spacer 39a. In particular, the end plate is machined such that shoulder 71 extends upwardly from a planar flange portion 72 approximately 0.2 inches and thus extends into a portion of central aperture 41a when the denuder assembly is assembled. Internal recess 40a is located in the upper surface of the shoulder portion, as most clearly shown in FIG. 14.

The stepped-end-plate configuration allows spacer 39a to have a greater thickness thus providing additional structural integrity and a simplified design. In particular, the thicker spacer allows a one-piece design which facilitates assembly of the denuder assembly. Advantageously, a gas inlet 73 and a gas outlet 74 can be readily drilled, with a countersinking if so desired, directly into spacer 39a thus providing a simple attachment means for fluidly coupling gas sample ingress and egress tubing with the gas channel. In operation and use, spacer 39a and end plates 38a are used in substantially the same manner as spacer 39 and end plates 38 discussed above.

For convenience in explanation and accurate definition in the appended claims, the terms "up" or "upper", "down" or "lower", "inside" and "outside", and similar terms are used to describe features of the present invention with reference to the positions of such features as displayed in the figures.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the are to best utilize the invention and various embodiments with various modifications as are suited to the particular use contemplated. It is intended that the scope of the invention be defined by the claims appended hereto and their equivalents.

What is claimed is:

1. A denuder for collection and removal of a gaseous analyte from a sample gas, said denuder comprising:
    a housing including an internal cavity;
    a sample gas inlet fluidly coupled with a sample gas source;
    a denuder liquid inlet fluidly coupled with a denuder liquid source; and
    a barrier sheet extending across said internal cavity and separating said internal cavity into a liquid reservoir and a gas flow-through channel fluidly coupled with and downstream of said sample gas inlet, said barrier sheet having a liquid-reservoir surface and a gas-channel surface and being permeable to the liquid and to solution space species derived from the analyte gas of interest; and
    a denuder liquid disposed in said liquid reservoir and permeating said barrier sheet to coat said gas-channel surface of said barrier sheet thereby allowing said denuder liquid on said gas-channel surface to contact the sample gas flowing within said gas flow-through channel and allowing the collected analyte to travel through said barrier sheet into said liquid reservoir.

2. The denuder of claim 1, wherein said housing is inert to the sample gas.

3. The denuder of claim 2, wherein at least a portion of said housing is formed of polytetrafluoroethylene, perfluoroalkoxy polytetrafluoroethylene or polycarbonate.

4. The denuder of claim 1, wherein said barrier sheet is a membrane.

5. The denuder of claim 4, wherein said membrane is hydrophilic.

6. The denuder of claim 5, wherein said membrane is formed of cellulose acetate, perfluorosulfonic acid, polyvinyl acetate, cellulose nitrate or cellulose ester.

7. The denuder of claim 1, wherein said barrier sheet is substantially planar.

8. The denuder of claim 1, wherein said barrier sheet is substantially vertically oriented.

9. The denuder of claim 1, wherein said barrier sheet is not substantially vertically oriented.

10. The denuder of claim 1, wherein said housing comprises a side plate having an internal recess defining a portion of said internal cavity, said liquid reservoir is at least partially defined by said internal recess and said liquid-reservoir surface while said gas flow-through channel is at least partially defined by said gas-channel surface and a remainder of said internal cavity.

11. The denuder of claim 10, wherein said side plate comprises a textured surface within said internal recess.

12. The denuder of claim 10, wherein said side plate includes a denuder liquid inlet positioned at one end of said internal recess fluidly coupled to said denuder liquid reservoir and a denuder liquid outlet positioned at an opposing end of said internal recess.

13. The denuder of claim 12, wherein said denuder liquid outlet is fluidly coupled with a detector for said analyte.

14. The denuder of claim 12, wherein said internal recess includes rectangular shape having V-shaped ends.

15. The denuder of claim 14, wherein said denuder liquid inlet is positioned adjacent a lower one of said V-shaped ends and said denuder liquid outlet is positioned adjacent an upper end of said V-shaped ends.

16. The denuder of claim 1, wherein said liquid reservoir includes a denuder liquid outlet fluidly coupled with a chromatography system.

17. The denuder of claim 16 in which said chromatography system comprises an ion chromatography system, fluorescence detection system or an absorbance detection system.

18. The denuder of claim 1 in which said gas flow-through channel has an outlet fluidly coupled with a particle detector, a particle collector or a particle analysis system.

19. The denuder of claim 1, wherein said housing comprises:
    a pair of parallel side plates, each side plate having an internal recess;
    a spacer disposed between said side plates and having a central aperture aligned with said internal recesses, said side plates and said spacer forming said housing wherein said central aperture and said internal recesses define said internal cavity; and
    a pair of barrier sheets separating said internal cavity into said gas flow-through channel and a pair of liquid reservoirs, each barrier sheet disposed between said spacer and a respective one of said parallel side plates.

20. A method for collection and removal of at least one gaseous analyte in a sample gas, said method comprising:
    providing a denuder having a barrier sheet extending across and separating an internal cavity in a housing into a gas flow-through channel and a liquid reservoir;
    providing a volume of denuder liquid in said liquid reservoir to permeate said barrier sheet and to coat a gas-channel surface of said barrier sheet with a film of said denuder liquid;
    flowing a sample gas through said gas flow-through channel whereby the film of said denuder liquid on said gas-channel surface contacts said sample gas flowing within said gas flow-through channel and the one analyte is collected and diffuses through said barrier sheet into said liquid reservoir; and
    removing said volume of denuder liquid, including the diffused one analyte, from said gas flow-though channel for analysis.

21. The method of claim 20, wherein said one analyte comprises an atmospheric gas soluble directly or upon reaction, in the aqueous liquid.

22. The method of claim 20, wherein said method further comprises the step of orienting said denuder such that said barrier sheet is vertically oriented.

23. The method of claim 20, wherein said method further comprises the step of orienting said denuder such that said barrier sheet is non-vertically oriented.

24. The method of claim 20, in which said denuder includes a pair of parallel side plates, each having an internal recess partially defining a respective liquid reservoir, and a spacer having a central aperture aligned with said internal recesses and partially defining said gas flow-through channel, wherein said method further comprises:

disposing a barrier sheet between said spacer and each one of said parallel side plates to separate the internal cavity into said gas flow-through channel and a pair of liquid reservoirs; and securing said spacer and said parallel side plates together.

25. The method of claim 24, wherein said method further comprises the step of trimming said barrier sheets along at least one of an outer periphery of said parallel side plates and an outer periphery of said spacer.

26. The method of claim 20 further comprising detecting the diffused analyte in said removed denuder liquid.

27. The method of claim 26 in which said sample gas comprises at least a second analyte and said method further comprises the step of separating said one and separate second analyte prior to detection.

28. The method of claim 27 in which said separation is performed by chromatography.

29. The method of claim 27 in which said method further comprises the step of fluorescence detection or absorbance detection.

30. The method of claim 20 in which said sample gas further comprises particles and said method further comprises analyzing the particles in said sample gas after exiting from said gas flow-through channel.

* * * * *